United States Patent [19]

Bender et al.

[11] Patent Number: 4,719,218

[45] Date of Patent: Jan. 12, 1988

[54] PYRROLO[1,2-A]IMIDAZOLE AND PYRROLO[1,2-A]PYRIDINE DERIVATIVES AND THEIR USE AS 5-LIPOXYGENASE PATHWAY INHIBITOR

[75] Inventors: Paul E. Bender, Cherry Hill, N.J.; Nabil Hanna, Berwyn, Pa.

[73] Assignee: SmithKline Beckman Corporation, Philadelphia, Pa.

[21] Appl. No.: 856,928

[22] Filed: Apr. 28, 1986

Related U.S. Application Data

[63] Continuation-in-part of Ser. No. 808,595, Dec. 12, 1985, abandoned.

[51] Int. Cl.$^4$ .................. A61K 31/415; C07D 471/04; C07D 487/04
[52] U.S. Cl. .................................... 514/300; 514/393; 548/324; 548/524; 548/558; 546/187; 546/199; 546/191; 546/193; 546/190; 546/197; 546/121; 546/271
[58] Field of Search ............... 546/271, 121, 187, 199; 548/324; 514/300, 393

[56] References Cited

U.S. PATENT DOCUMENTS

| | | |
|---|---|---|
| 3,823,239 | 7/1974 | Fox et al. .............................. 546/121 |
| 4,064,260 | 12/1977 | Cherkofsky et al. ................. 546/121 |
| 4,110,460 | 8/1978 | Baetz et al. .......................... 546/121 |
| 4,153,706 | 5/1979 | Bender et al. ........................ 546/121 |
| 4,175,127 | 11/1979 | Bender et al. ........................ 546/121 |
| 4,186,205 | 1/1980 | Bender et al. ........................ 546/121 |
| 4,263,311 | 4/1981 | Bender et al. ........................ 546/121 |
| 4,507,481 | 3/1985 | Davidson et al. ..................... 548/324 |

FOREIGN PATENT DOCUMENTS 154494  9/1985 European Pat. Off. ............ 546/121
1180202 2/1970 United Kingdom ................ 546/121
2039882 8/1980 United Kingdom ................ 546/121

OTHER PUBLICATIONS

Mohrle, H. et al., *Arch. Pharm.* 316, pp. 47–55 (1983).
Claxton, G. et al. *J. Med. Chem.*, 17, 3, 364–367 (1974).
*Chem. Abs.* 11994 q, vol. 82, p. 507 (1975).
Lantos et al., *J. Med. Chem.*, 27, 72–75 (1984).
Lantos et al., U.S. Ser. No. 856,246 filed Apr. 28, 1986.
Bender et al., *J. Med. Chem.*, 28, 1169–1177 (1985).
Bender et al., U.S. Ser. No. 856,875 filed Apr. 28, 1986.
Kano, S., *J. Pharm. Soc. Japan*, 92, 1, 55–58 (1972).
Andreani, A. et al., *Arch. Pharm.* (Weinheim), 315, 451–456 (1982).
Schoberl, A. et al., *Liebigs Ann. Chem.* 742, 85–97 (1970).
Lee, M. H., et al. *Biochemical Pharmacology*, 24, 1175–1178 (1975).
Andreani, A. et al. *Eur. J. Med. Chem.* 19, 3, 219–222 (1984).
Koyama, K. et al., *Oyo Yakura Pharmacometrics*, 26, 6, 869–876 (1983).

*Primary Examiner*—Henry R. Jiles
*Assistant Examiner*—J. Richter
*Attorney, Agent, or Firm*—Carol G. Canter; Nancy S. Mayer; Stuart R. Suter

[57] ABSTRACT

A method of inhibiting the production of 5-lipoxygenase products in an animal in need thereof which comprises administering an effective, 5-lipoxygenase pathway inhibiting amount of a 2(3)-(pyridyl)-3-(2)-substituted phenyl)-6,7-dihydro-[5H]-pyrrolo-[1,2-a]imidazole, a 2(3)-(pyridyl)-3(2)-(substituted phenyl)-5,6,7,8-tetrahydro-imidazo[1,2,-a]pyridine, or a pharmaceutically acceptable salt thereof, to such animal.

32 Claims, No Drawings

PYRROLO[1,2-A]IMIDAZOLE AND PYRROLO[1,2-A]PYRIDINE DERIVATIVES AND THEIR USE AS 5-LIPOXYGENASE PATHWAY INHIBITOR

CROSS REFERENCE TO RELATED APPLICATIONS

This is a continuation-in-part of Ser. No. 808,595, filed Dec. 12, 1985, which is now abandoned.

BACKGROUND OF THE INVENTION

This invention relates to novel compounds, pharmaceutical compositions and methods of inhibiting the 5-lipoxygenase pathway of arachidonic acid metabolism in an animal in need thereof which comprises administering to such animal an effective, 5-lipoxygenase pathway inhibiting amount of a 2(3)-(pyridyl)-3(2)-(substituted phenyl)-6,7-dihydro-[5H]-pyrrolo-[1,2-a]imidazole, a 2(3)-(pyridyl)-3(2)-(substituted phenyl)-5,6,7,8-tetrahydro-imidazo[1,2-a]pyridine or a pharmaceutically acceptable salt thereof.

Davidson et al., U.S. Pat. No. 4,507,481, issued Mar. 26, 1985, disclose compounds of the formula:

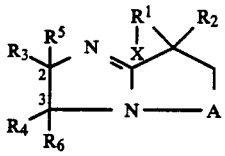

wherein:
 X is 0 or S(0)n;
 n is 0, 1 or 2;
 $R^1$ is H, lower alkyl, phenyl, benzyl or benzyl substituted with lower alkylamino, lower alkylamino, nitro, halo, hydroxy or lower alkoxy-;
 $R_2$ is H or $XR^1$;
 A is $CH_2$ or $CH_2CH_3$;
 $R_3$ and $R_4$ are independently selected from A, lower alkyl, aryl, aryl substituted with lower alkyl, amino, lower alkylamino, nitro, lower alkoxy, hydroxy or halogen; provided that at least one of $R_3$ and $R_4$ is aryl or substituted aryl; and
 $R_5$ and $R_6$ are each H or join to form a double bond at the 2,3-position.

Davidson et al. also disclose that such compounds are immunostimulants or immunosuppresants based on (a) their inhibiting or stimulating activity in a chemotaxis assay which measures the ability of a drug substance to influence the movement of murine macrophages responding to complement; (b) their immunosuppressing or activating activity in the Kennedy plaque assay in which an animal's humoral immune system is depressed artificially with 6-mercaptopurine. Neither the chemotaxis assay nor the Kennedy plaque assay is of any known utility for detecting or suggesting compounds which are inhibitors of the 5-lipoxygenase pathway. Davidson et al. also disclose that such compounds have antiinflammatory activity as determined by the carrageenan-induced paw edema assay in rats. As stated above, such assay has no known utility in detecting or suggesting compounds which are inhibitors of the 5-lipoxygenase pathway. Davidson et al. also disclose that such compounds have antiviral activity in mice with hepatitis; but such activity is of no known utility in detecting or suggesting compounds which are inhibitors of the 5-lipoxygenase pathway.

SUMMARY OF THE INVENTION

This invention relates to a compound of the formula

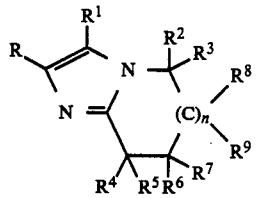

FORMULA (I)

wherein:
 n is 0 or 1;
 One of R or $R^1$ must be pyridyl and the other is selected from:
  (a) monosubstituted phenyl wherein said substitutent is selected from H, halo, $C_{1-3}$ alkoxy, $C_{1-3}$ alkylthio, $C_{1-4}$ alkyl, $C_{1-3}$ alkylsulfinyl, $C_{1-3}$ alkylsulfonyl, $C_{1-3}$ alkylamino, $C_{1-3}$ dialkylamino, $CF_3$, N-($C_{1-3}$ alkyl)-N-($C_{1-3}$ alkanamido), N-(azacyclo $C_{5-6}$ alkyl), prop-2-ene-1-oxy or 2,2,2-trihaloethoxy;
  (b) disubstituted phenyl wherein said substituents are the same and are selected from halo, $C_{1-3}$ alkoxy, $C_{1-3}$ alkylamino, $C_{1-3}$ dialkylamino, N-(azacyclo $C_{5-6}$ alkyl), 2,2,2-trihaloethoxy, prop-2-ene-1-oxy or hydroxy, or the disubstituents together form a methylene dioxy group; or
  (c) disubstituted phenyl wherein said substituents are not the same and are independently selected from halo, $C_{1-3}$ alkylamino, nitro, N-($C_{1-3}$ alkyl)-N- $C_{1-3}$ alkanamido), $C_{1-3}$ dialkylamino, amino, or N-(azacyclo $C_{5-6}$ alkyl); or
  (d) disubstituted phenyl wherein one of said substituents must be $C_{1-3}$ alkoxy, hydroxy, 2,2,2-trihaloethoxy or prop-2-ene-1-oxy and the other substituent is independently selected from halo, $C_{1-3}$ alkylamino, nitro, N-($C_{1-3}$ alkyl)-N-($C_{1-3}$ alkanamido), $C_{1-3}$ dialkylamino, amino, or N-(azacyclo $C_{5-6}$ alkyl); and $R^2$, $R^3$, $R^4$, $R^5$, $R^6$, $R^7$, $R^8$ and $R^9$ are H, or one or two of $R^2$, $R^3$, $R^4$, $R^5$, $R^6$, $R^7$, $R^8$ and $R^9$ are independently selected from H or $C_{1-2}$ alkyl; provided that:
   (1) when $R^1$ is 2 or 3-pyridyl and R is monosubstituted phenyl, the substituent selected from other than bromo, iodo, N-($C_{1-3}$ alkyl)-N-($C_{1-3}$ alkanamido), $C_{1-3}$ alkylthio, $C_{1-3}$ alkylsulfinyl, or $C_{1-3}$ alkylsulfonyl;
   (2) when $R^1$ is 2 or 3-pyridyl and R is disubstituted phenyl, the disubstituents are both selected from other than bromo, iodo, amino, hydroxy, nitro, or N-($C_{1-3}$ alkyl)-N-($C_{1-3}$ alkanamido);
   (3) when R is 2, 3 or 4-pyridyl and $R^1$ is monosubstituted phenyl, the substituent is selected from other than bromo, iodo, N-($C_{1-3}$ alkyl)-N-($C_{1-3}$ alkanamido), $C_{1-3}$ alkylthio, $C_{1-3}$ alkylsulfinyl, or $C_{1-3}$ alkylsulfonyl; and
   (4) when R is 2, 3 or 4-pyridyl and $R^1$ is disubstituted phenyl, the substituents are both selected from other than bromo, iodo, amino, hydroxy, nitro, or N-($C_{1-3}$ alkyl)-N-($C_{1-3}$ alkanamido);

or a pharmaceutically acceptable salt thereof.

The term "N-(azacyclo $C_{5-6}$ alkyl)" is used herein at all occurrences to mean pyrrolidino or piperidino.

This invention also relates to a pharmaceutical composition comprising a pharmaceutically acceptable carrier or diluent and an effective, non-toxic 5-lipoxygenase pathway inhibiting amount of a compound of the formula

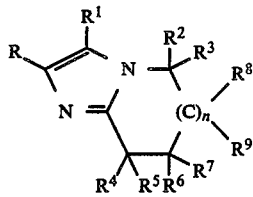

FORMULA (IA)

wherein:

n is 0 or 1;

One of R or $R^1$ must be pyridyl and the other is selected from:

(a) monosubstituted phenyl wherein said substituent is selected from H, halo, $C_{1-3}$ alkoxy, $C_{1-3}$ alkylthio, $C_{1-4}$ alkyl, $C_{1-3}$ alkylsulfinyl, $C_{1-3}$ alkylsulfonyl, $C_{1-3}$ alkylamino, $C_{1-3}$ dialkylamino, $CF_3$, N-(azacyclo $C_{5-6}$ alkyl), prop-2-ene-1-oxy or 2,2,2-trihaloethoxy;

(b) disubstituted phenyl wherein said substituents are the same and are selected from halo, $C_{1-3}$ alkoxy, $C_{1-3}$ alkylamino, $C_{1-3}$ dialkylamino, N-(azacyclo $C_{5-6}$ alkyl), 2,2,2-trihaloethoxy, prop-2-ene-1-oxy, or the disubstituents together form a methylene dioxy group;

(c) disubstituted phenyl wherein said substituents are not the same and are independently selected from $C_{1-3}$ alkylamino, $C_{1-3}$ dialkylamino, or N-(azacyclo $C_{5-6}$ alkyl); or (d) disubstituted phenyl wherein one of said substituents must be $C_{1-3}$ alkoxy, hydroxy, 2,2,2-trihaloethoxy or prop-2-ene-1-oxy and the other substituent is independently selected from halo, $C_{1-3}$ alkylamino, N-($C_{1-3}$ alkyl)-N-($C_{1-3}$ alkanamido), $C_{1-3}$ dialkylamino, amino, or N-(azacyclo $C_{5-6}$ alkyl); and $R^2$, $R^3$, $R^4$, $R^5$, $R^6$, $R^7$, $R^8$ and $R^9$ are H, or one or two of $R^2$, $R^3$, $R^4$, $R^5$, $R^6$, $R^7$, $R^8$ and $R^9$ are independently selected from H or $C_{1-2}$ alkyl; provided that:

(1) when $R^1$ is 2 or 3-pyridyl and R is monosubstituted phenyl, the substituent is selected from other than bromo, iodo, $C_{1-3}$ alkylthio, $C_{1-3}$ alkylsulfinyl, or $C_{1-3}$ alkylsulfonyl;

(2) when $R^1$ is 2 or 3-pyridyl and R is disubstituted phenyl, the disubstituents are both selected from other than bromo or iodo;

(3) when R is 2, 3 or 4-pyridyl and $R^1$ is monosubstituted phenyl, the substituents are selected from other than bromo, iodo, $C_{1-3}$ alkylthio, $C_{1-3}$ alkylsulfinyl, or $C_{1-3}$ alkylsulfonyl; and (4) when R is 2, 3 or 4-pyridyl and $R^1$ is disubstituted phenyl, the substituents are both selected from other than bromo or iodo;

or a pharmaceutically acceptable salt thereof.

This invention also relates to a method of treating a 5-lipoxygenase pathway mediated disease in an animal in need thereof which comprises administering to such animal an effective, non-toxic 5-lipoxygenase pathway inhibiting amount of a compound of Formula (IA), or a pharmaceutically acceptable salt thereof.

This invention also relates to a compound of the formula:

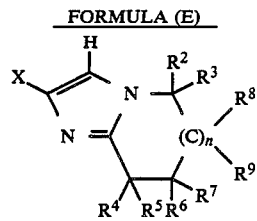

FORMULA (E)

n is 0 or 1;

$R^2$, $R^3$, $R^4$, $R^5$, $R^6$, $R^7$, $R^8$ and $R^9$ are H, or one or two of $R^2$, $R^3$, $R^4$, $R^5$, $R^6$, $R^7$, $R^8$ and $R^9$ are independently selected from H or $C_{1-2}$ alkyl;

X is selected from:

(a) pyridyl;

(b) monosubstituted phenyl, wherein said substituent is selected from halo, $C_{1-3}$ alkoxy, amino, hydroxy, $C_{1-3}$ alkylthio, $C_{1-4}$ alkyl, $C_{1-3}$ alkylamino, $C_{1-3}$ dialkylamino, $CF_3$, N-($C_{1-3}$ alkanamido), N-($C_{1-3}$ alkyl)-N-($C_{1-3}$ alkanamido), N-(azacyclo $C_{5-6}$ alkyl), prop-2-ene-1-oxy or 2,2,2-trihaloethoxy;

(c) disubstituted phenyl wherein said substituents are the same and are selected from halo, $C_{1-3}$ alkoxy, $C_{1-3}$ alkylamino, $C_{1-3}$ dialkylamino, amino, N-(azacyclo $C_{5-6}$ alkyl), 2,2,2-trihaloethoxy, prop-2-ene-1-oxy, hydroxy, or the disubstituents together form a methylene dioxy group; or (d) disubstituted phenyl wherein said substituents are not the same and are independently selected from halo, $C_{1-3}$ alkylamino, nitro, N-($C_{1-3}$ alkanamido), N-($C_{1-3}$ alkyl)-N-($C_{1-3}$ alkanamido), $C_{1-3}$ dialkylamino, amino or N-(azacyclo $C_{5-6}$ alkyl), and (e) disubstituted phenyl wherein one of said substituents must be $C_{1-3}$ alkoxy, hydroxy, 2,2,2-trihaloethoxy or prop-2-ene1-oxy and the other substituent is independently selected from halo, $C_{1-3}$ alkylamino, nitro, N-($C_{1-3}$ alkyl)-N-($C_{1-3}$ alkanamido), $C_{1-3}$ dialkylamino, amino, or N-(azacyclo $C_{5-6}$ alkyl);

provided that when n is 1, and $R^2$, $R^3$, $R^4$, $R^5$, $R^6$, $R^7$, $R^8$ and $R^9$ are H, X is other than 2,4-dimethoxyphenyl or 4-amino-phenyl;

or a pharmaceutically acceptable salt thereof.

This invention also relates to a compound of the formula:

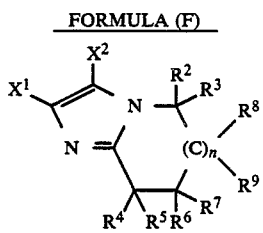

FORMULA (F)

wherein:

n is 0 or 1, $R^2$, $R^3$, $R^4$, $R^5$, $R^6$, $R^7$, $R^8$, $R^9$ are all H, or one or two of $R^2$, $R^3$, $R^4$, $R^5$, $R^6$, $R^7$, $R^8$ and $R^9$, are independently selected from H or $C_{1-2}$ alkyl;

$X^2$ is 4-(1,4-dihydro)pyridyl substituted with N-($C_{1-8}$ alkanoyl), N-($C_{1-8}$ alkoxycarbonyl), N-(benzoyl), N-(phenoxycarbonyl), N-(phenylacetyl), or N-(benzyloxycarbonyl);

$X^1$ is selected from
- (a) monosubstituted phenyl wherein said substituent is selected from H, halo, $C_{1-3}$ alkoxy, $C_{1-3}$ alkylthio, $C_{1-4}$ alkyl, $CF_3$ N-($C_{1-3}$ alkyl)-N-($C_{1-3}$ alkanamido), $C_{1-3}$ dialkylamino, $CF_3$, N-(azacyclo $C_{5-6}$ alkyl), prop-2-ene-1-oxy or 2,2,2-trihaloethoxy;
- (b) disubstituted phenyl wherein said substitutents are the same and are selected from halo, $C_{1-3}$ alkoxy, $C_{1-3}$ dialkylamino, N-(azacyclo $C_{5-6}$ alkyl), 2,2,2-trihaloethoxy, or prop-2-ene-1-oxy, or the disubstituents together form a methylene dioxy group; or
- (c) disubstituted phenyl wherein said substituents are not the same and are independently selected from halo, nitro, N-($C_{1-3}$ alkyl)-N-($C_{1-3}$ alkanamido), $C_{1-3}$ dialkylamino, or N-(azacyclo $C_{5-6}$ alkyl; or
- (d) disubstituted phenyl wherein one of said substituents must be $C_{1-3}$ alkoxy, hydroxy, 2,2,2-trihaloethoxy or prop-2-ene-1-oxy and the other substituent is independently selected from halo, $C_{1-3}$ alkylamino, nitro, N-($C_{1-3}$ alkyl)-N-($C_{1-3}$ alkanamido), $C_{1-3}$ dialkylamino, amino, or N-(azacyclo $C_{5-6}$ alkyl);

or a pharmaceutically acceptable salt thereof.

This invention also relates to a compound of the formula:

FORMULA (G)

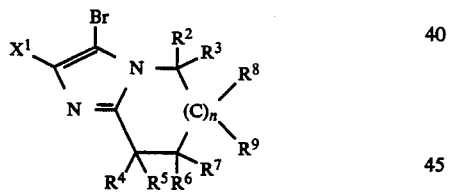

wherein:
n is 0 or 1,
$R^2$, $R^3$, $R^4$, $R^5$, $R^6$, $R^7$, $R^8$ and $R^9$ are all H, or one or two of $R^2$, $R^3$, $R^4$, $R^5$, $R^6$, $R^7$, $R^8$, and $R^9$ are independently selected from H or $C_{1-2}$ alkyl; and $X^1$ is selected from
- (a) monosubstituted phenyl wherein said substituent is selected from H, fluoro, chloro, $C_{1-3}$ alkoxy, $C_{1-4}$ alkyl, $C_{1-3}$ dialkylamino, $CF_3$, $C_{1-3}$ alkylamino, N-(azacyclo $C_{5-6}$ alkyl), prop-2-ene-1-oxy or 2,2,2-trihaloethoxy;
- (b) disubstituted phenyl wherein said substituents are the same and are selected from fluoro, chloro, $C_{1-3}$ alkoxy, $C_{1-3}$ dialkylamino, N-(azacyclo $C_{5-6}$ alkyl), 2,2,2-trihaloethoxy, prop-2-ene-1-oxy, or the disubstituents together form a methylene dioxy group;
- (c) disubstituted phenyl wherein said substituents are not the same and are independently selected from fluoro, chloro, $C_{1-3}$ alkylamino, $C_{1-3}$ dialkylamino, or N-(azacyclo $C_{5-6}$ alkyl), or
- (d) disubstituted phenyl wherein one of said substituents must be $C_{1-3}$ alkoxy, 2,2,2-trihaloethoxy or prop-2-ene-1-oxy and the other substituent is independently selected from fluoro, chloro, $C_{1-3}$ alkylamino, $C_{1-3}$ dialkylamino, or N-(azacyclo $C_{5-6}$ alkyl;

or a pharmaceutically acceptable salt thereof.

This invention relates to compounds of the formula

FORMULA (H)

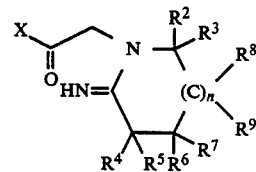

wherein:
n is 0 or 1;
$R^2$, $R^3$, $R^4$, $R^5$, $R^6$, $R^7$, $R^8$, and $R^9$ are H, or one or two of $R^2$, $R^3$, $R^4$, $R^5$, $R^6$, $R^7$, $R^8$ and $R^9$ are independently selected from H or $C_{1-2}$ alkyl;
X is selected from:
- (a) pyridyl;
- (b) monosubstituted phenyl, wherein said substituent is selected from H, halo, $C_{1-3}$ alkoxy, $C_{1-3}$ alkylthio, $C_{1-4}$ alkyl, N-($C_{1-3}$ alkanamido), $C_{1-3}$ dialkylamino, $CF_3$, N-(azacyclo $C_{5-6}$ alkyl);
- (c) disubstituted phenyl wherein said substituents are the same and are selected from halo, $C_{1-3}$ alkoxy, N-($C_{1-3}$ alkanamido), $C_{1-3}$ dialkylamino, N-(azacyclo $C_{5-6}$ alkyl), or the disubstituents together form a methylene-dioxy group;
- (d) disubstituted phenyl wherein said substituents are not the same and are independently selected from halo, nitro, N-($C_{1-3}$ alkanamido), $C_{1-3}$ alkoxy, $C_{1-3}$ dialkylamino, or N-(azacyclo $C_{5-6}$ alkyl); or
- (e) disubstituted phenyl wherein one of said substituents must be $C_{1-3}$ alkoxy, hydroxy, 2,2,2-trihaloethoxy or prop-2-ene-1-oxy and the other substituent is independently selected from halo, nitro, N-($C_{1-3}$ alkyl)-N-($C_{1-3}$ alkanamido), $C_{1-3}$ dialkylamino, or N-(azacyclo $C_{5-6}$ alkyl);

or a pharmaceutically acceptable salt thereof.

DETAILED DESCRIPTION OF THE INVENTION

It will be apparent to one of skill in the art that all of the compounds of Formula (IA) are encompassed by the scope of the compounds of Formula (I). The compounds of Formula (I) which are not encompassed by the scope of Formula (IA) are useful as intermediates in the preparation of the compounds of Formula (IA). All of the compounds of Formula (IA) are useful in inhibiting the 5lipoxygenase pathway of arachidonic acid metabolism in an animal in need thereof.

The compounds of Formula (I) can be prepared according to the following synthetic route:

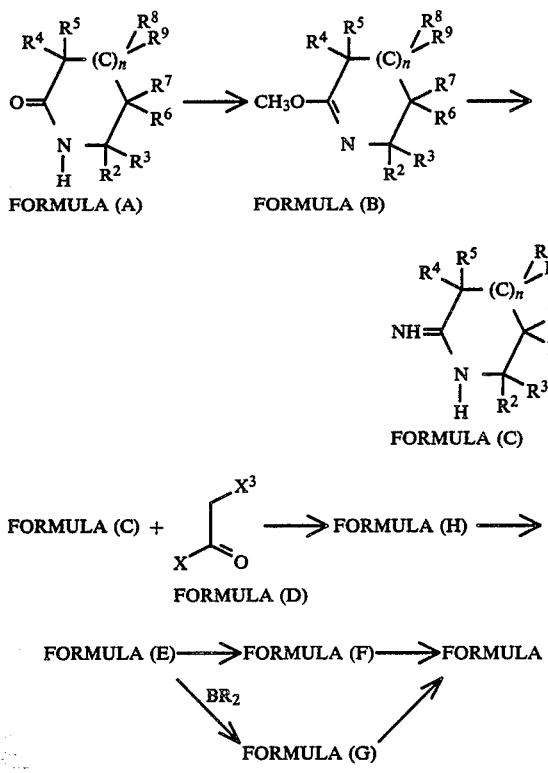

FORMULA (A)  FORMULA (B)

FORMULA (C)

FORMULA (C) + FORMULA (D) → FORMULA (H) →

FORMULA (E) → FORMULA (F) → FORMULA (I)
          ↘ BR₂           ↗
            FORMULA (G)

All the compounds of Formula (E), Formula (F), Formula (G) and Formula (H) are useful as intermediates in the preparation of compounds of Formula (I). All of the necessary compounds of Formula (A), Formula (B), Formula (C) and Formula (D) can be obtained from commercial sources or are preparable by conventional techniques such as those set out herein.

Compounds of Formula (B), wherein n, $R^2$, $R^3$, $R^4$, $R^5$, $R^6$, $R^7$, $R^8$ and $R^9$ are as defined above, can be prepared by 0-alkylation of the corresponding 2-piperidone or 2-pyrrolidone of Formula (A), wherein n, $R^2$, $R^3$, $R^4$, $R^5$, $R^6$, $R^7$, $R^8$ and $R^9$ are as defined above, with dimethylsulfate according to the method of Wick et al., *Helv. Chim Acta*, 54, 513 (1971). The necessary compounds of Formula (A) are commercially available or are prepared by known techniques. Compounds of Formula (C) wherein n, $R^2$, $R^3$, $R^4$, $R^5$, $R^6$, $R^7$, $R^8$, and $R^9$ are as defined above, can be prepared by treatment of the corresponding compound of Formula (B) with ammonium chloride in absolute ethanol according to the method of Etienne et al., *Compt. Rend.*, 259, 2660 (1964). Compounds of Formula (C) wherein n is 1 or 2 and $R^2$, $R^3$, $R^4$, $R^5$, $R^6$, $R^7$, $R^8$ and $R^9$ are H are preferably prepared as described by the method of Moriconia and Cevasco, *J. Org. Chem.*, 33, 2109 (1968) as their hydrohalide salts and liberated to the bases with concentrated aqueous NaOH. Compounds of Formula (D), wherein $X^3$ is Br and X is as defined above, are commercially available or are prepared by treatment of the correspondingly substituted acetophenone in $CH_2Cl_2$, $CHCl_3$ or acetic acid with one equivalent of bromine [See, Langley, *Org. Syn. Coll.*, 1, 127 (1944); Cowper et al., *Org. Syn. Coll.*, 2, 480 (1943); and Lorenzin, et al., *J. Org. Chem.*, 32, 4008 (1967)], or alternatively, by reaction in chloroform-ethyl acetate with a suspension of copper (II) bromide by the method of King and Ostrum, *J. Org. Chem.*, 29, 3459 (1964). The necessary acetophenones are commercially available or preparable by known techniques. Alternatively the Formula (D) compounds, wherein $X^3$ is chloro and X is (a) 4 monosubstituted phenyl where the substituent is selected from H, halo, $C_{1-4}$ alkyl, $C_{1-3}$ alkylthio, $C_{1-3}$ alkoxy, or (b) 3,4-disubstituted phenyl wherein the substituents are the same and are selected from $C_{1-3}$ alkoxy, methylenedioxy, or where the substituents are independently selected from halo or $C_{1-3}$ alkoxy, can be prepared by acylating the corresponding mono- or disubstituted benzene by Friedel Crafts reaction with 2-chloroacetylchloride and $AlCl_3$, by the method of Joshi et al., *J. Heterocyclic Chem.*, 16, 1141 (1979). Preferably, compounds of Formula (E) are prepared from their corresponding compound of Formula (H). Compounds of Formula (H) serve as intermediates in the preparation of compounds of Formula (E). Compounds of Formula (H) are prepared by treatment of a solution of a substituted Formula (D) compound, such as a 2-haloacetophenone, or a 2,3, or 4-bromoacetylpyridine, both of which are described by Taurins et al., *J. Heterocyclic Chem.*, 7, 1137 (1970), in a neutral, preferably nonpolar solvent with one molar equivalent of the corresponding Formula (C) compound, maintaining the temperature at or below 25° C. The resulting crystalline Formula (H) hydrohalide salts are converted to Formula (E) compounds by refluxing in water. Compounds of Formula (E) serve as intermediates in the preparation of the compounds of Formula (I). Alternatively, compounds of Formula (E) are prepared by treatment of a solution of the 2-iminopyrrolidine or 2-iminopiperidine with a substituted 2-bromoacetophenone of Formula (D), either in a polar organic solvent, such as DMF or ethanol, or in a nonpolar chlorinated hydrocarbon, followed by removing all or most of the solvent and refluxing the residue in aqueous solution.

Compounds of Formula (I) where R is phenyl or substituted phenyl, and $R^1$ is 4-pyridyl are preferably prepared in two steps by a modification of the method of Lantos et al., U.S. patent application Ser. No. 737,157, filed May 29, 1985. In the first step, the corresponding compound of Formula (E) is treated, preferably at 20°-25° C., with pyridine and an acyl halide or a haloacyl ester such as acetyl bromide, benzoylchloride, benzyl chloroformate, or preferably ethyl chloroformate, in a solvent in which the reactants are soluble and inert to form the compound of Formula (F). Compounds of Formula (F) serve as intermediates in the preparation of the compounds of Formula (I). In the second step, the Formula (F) compound, a dihydropyridine product, is deacylated and aromatized with sulfur in refluxing decalin, tetralin, p-cymene or xylene, or preferably with potassium tert.-butoxide in tert.-butanol with $O_2$ gas at reflux for 15 minutes to the afford the corresponding compound of Formula (I).

The same Formula (E) compounds used to prepare the 4-pyridyl Formula (I) compounds are employed to prepare the 2-pyridyl and 3-pyridyl Formula (I) compounds. Treatment of the Formula (E) compounds with bromine by the procedure of Kano, *Yakugaku Zasshi*, 92, 51 (1972), results in 3-bromination to afford the 3-bromo-2-(substituted phenyl)-6,7-dihydro-(5H)-pyrrolo(1,2-a)imidazoles and 3-bromo-2-(substituted phenyl)-5,6,7,8-tetrahydro-imidazo(1,2-a)pyridines compounds of Formula (G). The compounds of Formula (G) serve as intermediates in the preparation of compounds of Formula (I). These Formula (G) compounds are treated with n-butyl lithium (n-BuLi) in THF to afford their 3-lithio derivatives by halogen-metal interchange. Transmetallation of the 3-lithio compounds with MgBr2 or ZnCl2 to the corresponding magnesium or zinc compounds, according to the method of Negishi et al., *J. Org. Chem.*, 42, 1821, (1977), provides good coupling to 2- or 3- bromopyridine in the presence of PdCl2(1,4-bis(diphenylphosphino)butane) catalyst, a bidentate Pd (II) catalyst, using the method of Kumada et al., *Tetrahedron Letters,* 22, 5319 (1981). Alternatively the Formula (G) compounds may be coupled to the 2 or 3-metalated pyridine employing this bidentate Pd (II) catalyst, or the corresponding Ni(II) Cl2 (1,2-bis(diphenylphosphino) ethane catalyst [see, Pridgen, *J. Org. Chem.*, 47, 4319 (1982)]. By either of these routes, Formula (I) compounds are obtained where $R^1$ is 2-pyridyl or 3-pyridyl.

Regioisomers of Formula (I) compounds where $R^1$ is substituted phenyl, or 2,3 or 4-pyridyl and R is 2, 3, and 4-pyridyl are obtained from compounds of Formula (E) where X is 2,3, or 4-pyridyl. Compounds of Formula (E) where X is 2, 3 or 4-pyridyl are prepared by treatment of a 2, 3, or 4-bromoacetylpyridine hydrobromide salt of Formula (D), wherein R is 2, 3 or 4-pyridyl [prepared as described by Taurins et al., *J. Het Chem.*, 7, 1137 (1970)] with 2-3 equivalents of the 2-iminopyrrolidine or 2-iminopiperidine by the procedure used to prepare the other compounds of Formula (E) described above. 3-Bromination, by the procedure of Kano cited above, affords the corresponding Formula (G) compounds. Metalation of the Formula (G) compounds via halogen-metal interchange with n-BuLi, transmetallation with MgBr2 and coupling to the substituted bromobenzene or (2,3, or 4)-bromopyridine in the presence of the bidentate phosphine-palladium or nickel complex as described above affords the desired regioisomers of Formula (I) and the bis(pyridyl) compounds of Formula (I). Alternatively the metalated pyridine or substituted benzene may be coupled to the Formula (G) compounds employing the catalysts as described above.

Compounds of Formula (I) where R or $R^1$ are $C_{1-3}$ alkylsulfinyl substituted phenyl are prepared by treatment of one equivalent of the corresponding compound of Formula (I) where R or $R^1$ are $C_{1-3}$ alkylmercaptophenyl, with one equivalent of an oxidizing agent (preferably, 3-chloroperbenzoic acid) per mercapto function, in an inert solvent. Compounds of Formula (I) wherein R or $R^1$ are $C_{1-3}$ alkylsulfonyl substituted phenyl are prepared by treatment of one equivalent of the corresponding $C_{1-3}$ sulfinyl Formula (I) compound with ⅔ equivalent of KMnO4 per sulfinyl function in aqueous solution by the method of Chatterway et al., *J. Chem. Soc.* 1352 (1930).

N-($C_{1-3}$ alkanamido) and N-($C_{1-3}$ alkyl)-N-($C_{1-3}$ alkanamido)phenyl substituted acetophenones, and in some cases the Formula (E), and Formula (I) compounds, are prepared by acylation of the corresponding amino and N-($C_{1-3}$ alkylamino) compounds with the alkanoic acid anhydride or chloride in pyridine. Another alternative preparation of the N-($C_{1-3}$ alkyl)-N-($C_{1-3}$ alkanamido) phenyl substituted Formula (E) and Formula (I) compounds is the alkylation of the corresponding N-($C_{1-3}$ alkanamido) substituted compounds with sodium hydride and a $C_{1-3}$ alkyl bromide or iodide in dimethyl formamide.

Aminophenyl substituted Formula (E) and Formula (I) compounds are prepared either by hydrolysis of the corresponding N-($C_{1-3}$ alkanamido) compounds in refluxing 6 N mineral acid or by catalytic reduction of the corresponding nitro compounds.

N-($C_{1-3}$ alkylamino)phenyl substituted Formula (E), Formula (G), and Formula (I) compounds are preferably prepared by acid catalyzed hydrolysis of the corresponding N-($C_{1-3}$ alkyl)-N-($C_{1-3}$ alkanamido) compounds of Formula (E), Formula (G) and Formula (I), respectively, prepared as described above for the aminophenyl substituted compounds, or alternatively, either by (a) reduction of the corresponding N-($C_{1-3}$ alkanamido) compounds with borane or borane dimethylsulfide complex in THF by the method of Brown, "Organic Synthesis via Boranes", John Wiley and Sons, (1975), or (b) by cleavage of the corresponding N,N-(di $C_{1-3}$ alkylamino)phenyl substituted Formula (E) and Formula (I) compounds with cyanogen bromide in the Von Braun reaction [see, Hageman Org. Reactions, Vol. 7, 198 (1953)].

N,N-(di $C_{1-3}$ alkylamino)phenyl substituted Formula (E) and Formula (I) compounds are alternatively prepared either by reduction of the corresponding N-($C_{1-3}$ alkyl)-N-($C_{1-3}$ alkanamido) compounds of Formula (E) and Formula (I) with borane as described above for the N-($C_{1-3}$ alkylamino)phenyl substituted compounds N-(azacyclo $C_{5-6}$ alkyl)phenyl substituted Formula (E) and Formula (I) compounds are alternatively prepared by cyclodialkylation of the corresponding aminophenyl compounds with dibromobutane or dibromopentane and anhydrous potassium carbonate in an inert solvent such as dimethylformamide.

Compounds of Formula (E) where X is 2,2,2-trihaloethoxy or prop-2-ene-1-oxy substituted phenyl are prepared by alkylation of the appropriate phenols of Formula (E) with trifluoromethylsulfonic acid 2,2,2-trifluoroethyl ester or allyl bromide respectively as described by Bender et al., *J. Med. Chem.*, 28, 1169 (1985), for preparation of compounds No. 23 and 33 described therein. Appropriately substituted mono and dihydroxy phenyl compounds of Formula (E) and Formula (I) are obtained by treatment of their respective correspondingly substituted methoxy derivatives with HBr in acetic acid, or preferably with BBr3 in $CH_2Cl_2$ by the method described by Bender et al., *J. Med. Chem.*, 28, 1169 (1985), for the preparation of compound No. 14 described therein.

Pharmaceutically acceptable salts and their preparation are well known to those skilled in pharmaceuticals. Pharmaceutically acceptable salts of the compounds of Formula (I) which are useful in the present invention include, but are not limited to, maleate, fumarate, lactate, oxalate, methanesulfonate, ethanesulfonate, benzenesulfonate, tartrate, citrate, hydrochloride, hydrobromide, sulfate and phosphate salts. Preferred pharmaceutically acceptable salts of the compounds of Formula (I) include hydrochloride and hydrobromide salts, and such salts can be prepared by known techniques such as the method of Bender et al., U.S. Pat. No. 4,175,127, the disclosure of which is hereby incorporated by reference.

It has now been discovered that the compounds of Formula (IA) are useful for treating disease states mediated by the 5-lipoxygenase pathway of arachidonic acid metabolism in an animal, including mammals, in need thereof. The discovery that the compounds of Formula (IA) are inhibitors of the 5-lipoxygenase pathway is based on the effects of the compounds of Formula (IA) on tissue inflammation in vivo and on the production of 5-lipoxygenase products by inflammatory cells in vitro in assays, some of which are described in the Examples. In summary, such assays reveal that the compounds of Formula (IA) display anti-inflammatory activity in arachidonic acid-induced inflammation in the mouse ear model. The cyclooxygenase inhibitor, indomethacin, did not reduce inflammation in these assays. The 5-lipoxygenase pathway inhibitory action of the compounds of Formula (IA) was confirmed by showing that they impaired the production of 5-lipoxygenase products such as leukotriene $B_4$ (di-HETE) and 5-HETE production by RBL-1 cells.

The pathophysiological role of arachidonic acid metabolites has been the focus of recent intensive studies. In addition to the well-described phlogistic activity (i.e. general inflammatory activity) of prostaglandins, the more recent description of similar activity for eicosanoids has broadened the interest in these products as mediators of inflammation [See, O'Flaherty, *Lab. Invest.*, 47, 314–329 (1982)]. The reported discovery of potent chemotactic and algesic activity for $LTB_4$ [see, Smith, *Gen. Pharmacol.*, 12, 211–216 (1981) and Levine et al., *Science*, 225, 743–745 (1984)], together with known $LTC_4$ and $LTD_4$-mediated increase in capillary permeability [see, Simmons et al., *Biochem. Pharmacol.*, 32, 1353–1359 (1983), Veno et al., *Prostaglandins*, 21, 637–647 (1981), and Camp et al., *Br. J. Pharmacol.*, 80, 497–502 (1983)], has led to their consideration as targets for pharmacological intervention in both the fluid and cellular phases of inflammatory diseases.

The pharmacology of several inflammatory model systems has attested to the effectiveness of corticosteroids in reducing the cellular infiltration. These results, and the observation that corticosteroids inhibit the generation of both cyclooxygenase and lipoxygenase products, suggest that such dual inhibitors may effectively reduce both the fluid and cellular phases of the inflammatory response since selective cyclooxygenase inhibitors do not reliably inhibit cell influx into inflammatory sites [See, Vinegar et al., *Fed. Proc.*, 35, 2447–2456 (1976), Higgs et al., *Brit. Bull.*, 39, 265–270 (1983), and Higgs et al., *Prostaglandins, Leukotrienes and Medicine*, 13, 89–92 (1984)]. The observations outlined above cogently argue that a dual inhibitor of arachidonic acid metabolism would be a more effective antiinflammatory agent than an inhibitor of cyclooxygenase only. Under optimal conditions, it is likely that an agent with preferential lipoxygenase inhibitory activity would not share the ulcerogenic liability of cyclooxygenase inhibitors or the toxicity of corticosteroids.

Recent clinical data also support the enthusiasm for inhibitors of the 5-lipoxygenase pathway in a variety of inflammatory diseases in which granulocyte and/or monocyte infiltration is prominent. The reported demonstration of elevated levels of $LTB_4$ in rheumatoid arthritic joint fluid [See, Davidson et al., *Ann. Rheum. Dis.*, 42, 677–679 (1983)] also suggests a contributing role for arachidonic acid metabolites in rheumatoid arthritis. The recently reported preliminary observation of efficacy, including remission, reported with sulfasalazine treatment of rheumatoid arthritic patients [See Neumann et al., *Brit. Med. J.*, 287, 1099–1102 (1983)] illustrates the utility of inhibitors of the 5-lipoxygenase pathway in rheumatoid arthritis.

Sulfasalazine, which is used for treatment of ulcerative colitis, has been reported to inhibit $LTB_4$ and 5-HETE production in vitro [See, Stenson et al., *J. Clin. Invest.*, 69, 494–497 (1982)]. This observation, coupled with the fact that it has been reported that inflamed gastrointestinal mucosa from inflammatory bowel disease patients showed increased production of $LTB_4$ [See, Sharon et al., *Gastroenterol.*, 84, 1306 (1983)], suggests that sulfasalazine can be effective by virtue of inhibition of production of chemotactic eicosanoids (such as the 5-lipoxygenase pathway product known as $LTB_4$). The observations serve to underscore utility of inhibitors of the 5-lipoxygenase pathway in inflammatory bowel disease.

Another area of utility for an inhibitor of the 5-lipoxygenase pathway is in the treatment of psoriasis. It was demonstrated that involved psoriatic skin had elevated levels of $LTB_4$ [See, Brain et al., *Lancet*, 19, Feb. 19, 1983]. The promising effect of benoxaprofen on psoriasis [See, Allen et al., *Brit. J. Dermatol.*, 109, 126–129 (1983)], a compound with in vitro lipoxygenase inhibitory activity on psoriasis, lends support to the concept that inhibitors of the 5-lipoxygenase pathway can be useful in the treatment of psoriasis.

Lipoxygenase products have been identified in exudate fluids from gouty patients. This disorder is characterized by massive neutrophil infiltration during the acute inflammatory phases of the disease. Since a major 5-lipoxygenase product, $LTB_4$, is produced by neutrophils, it follows that inhibition of the synthesis of $LTB_4$ can block an amplification mechanism in gout.

Another area in which inhibitors of the 5-lipoxygenase product can have utility is in myocardial infarction. Studies in dogs with the dual inhibitor, BW755-C, demonstrated that the area of infarction following coronary occlusion was reduced, and such reduction was attributed to inhibition of leukocyte infiltration into the ischaemic tissue [See, Mollane et al., *J. Pharmacol. Exp. Therap.*, 228, 510–522 (1984)].

Yet another area of utility for inhibitors of the 5-lipoxygenase pathway is in the area of prevention of rejection of organ transplants. [See, e.g., Foegh et al., *Adv. Prostaglandin, Thromboxane, and Leukotriene Research*, 13, 209–217 (1983).]

Yet another utility for inhibitors of the 5-lipoxygenase pathway is in the treatment of tissue trauma. [See, e.g., Denzlinger et al. *Science*, 230 (4723), 330–332 (1985)].

Furthermore, another area of utility for inhibitors of the 5-lipoxygenase pathway is in the treatment of inflammatory reaction in the central nervous system, including multiple sclerosis. [See, e.g., Mackay et al., *Clin. Exp. Immunology*, 15, 471–482 (1973)].

Additionally, another area of utility for inhibitors of the 5-lipoxygenase pathway is in the treatment of asthma. [See, e.g., Ford-Hutchinson, *J. Allergy Clin. Immunol.*, 74, 437–440 (1984)].

This invention also relates to a pharmaceutical composition comprising an effective, 5-lipoxygenase pathway inhibiting amount of a compound of Formula (IA) or a pharmaceutically acceptable salt thereof and a pharmaceutically acceptable carrier or diluent.

The pharmaceutically effective compounds of this invention are administered in conventional dosage forms prepared by combining a compound of Formula (IA) ("active ingredient") in an amount sufficient to produce 5-lipoxygenase pathway inhibiting activity with standard pharmaceutical carriers according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. a liquid carrier is used, the preparation will be in the form of a syrup, emulsion, soft gelatin capsule, sterile injectable liquid such as an ampule or nonaqueous liquid suspension.

To obtain a stable water soluble dose form, a pharmaceutically acceptable salt of a compound of Formula (IA) is dissolved in an aqueous solution of an organic or inorganic acid, such as a 0.3 M solution of succinic acid or, preferably, citric acid.

Preferably, each parenteral dosage unit will contain the active ingredient [i.e., the compound of Formula (IA)] in an amount of from about 50 mg. to about 500 mg. Preferably, each oral dosage will contain the active ingredient in an amount of from about 100 mg to about 1000 mg.

The compounds of Formula (IA) may also be administered topically to a mammal in need of the inhibition of the 5-lipoxygenase pathway of arachidonic acid metabolism. Thus, the compounds of Formula (IA) may be administered topically in the treatment or prophylaxis of inflammation in an animal, including man and other mammals, and may be used in the relief or prophylaxis of 5-lipoxygenase pathway mediated diseases such as rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The amount of a compound of Formula (IA) (hereinafter referred to as the active ingredient) required for therapeutic effect on topical administration will, of course, vary with the compound chosen, the nature and severity of the inflammatory condition and the animal undergoing treatment, and is ultimately at the discretion of the physician. A suitable anti-inflammatory dose of an active ingredient is 1.5 $\mu$g to 500 mg of base for topical administration, the most preferred dosage being 1 $\mu$g to 1000 $\mu$g, for example 5 to 25 $\mu$g administered two or three times daily.

By topical administration is meant non-systemic administration and includes the application of a compound of Formula (IA) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as prolylene glycol or macrogols. The formulation may incorporate any suitable surface active agent such as an anionic, cationic or non-ionic sulfactant such as sorbitan esters or polyoxyethylene derivatives thereof. Suspending agents such as natural gums, cellulose derivatives or inorganic materials such as silicaceous silicas, and other ingredients such as lanolin, may also be included.

The compounds of Formula (IA) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (IA) administered by inhalation is from about 10 mg to about 100 mg per day.

This invention also relates to a method of treating a disease state which is mediated by the 5-lipoxygenase pathway in an animal in need thereof, including humans and other mammals, which comprises administering to such animal an effective, 5-lipoxygenase pathway inhibiting amount of a Formula (IA) compound. By the term "treating" is meant either prophylactic or therapeutic therapy. By the term "mediated" is meant caused by or exacerbated by. Such Formula (IA) compound can be administered to such animal in a conventional dosage form prepared by combining the Formula (IA) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The Formula (IA) compound is administered to an animal in need of inhibition of the 5-lipoxygenase pathway in an amount sufficient to inhibit the 5-lipoxygenase pathway. The route of administration may be oral, parenteral, by inhalation or topical. The term parenteral as used herein includes intravenous, intramuscular, subcutaneous, intrarectal, intravaginal or intraperitoneal administration. The subcutaneous and intramuscular forms of parenteral administration are generally preferred. The daily parenteral dosage regimen will preferably be from about 50 mg to about 1000 mg per day. The daily oral dosage regimen will preferably be from about 150 mg to about 2000 mg per day. It will be recognized by one of skill in the art that the optimal quantity and spacing of individual dosages of the Formula (IA) compound will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the Formula (IA) compound given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following examples are, therefore, to be construed as merely illustrative and not a limitation of the scope of the present invention in any way.

Temperature is in degrees Centigrade (°C.).

EXAMPLE I 2-(4-Fluorophenyl)-6,7-dihydro-(5H)-pyrrolo[1,2-a]imidazole (Formula (E) Compound)

Method A.

A stirred solution of 15 g (87 mmoles) of 2-chloro4-fluoroacetophenone in 75 ml of SD 30 alcohol was treated at 25° C. with 10.65 g (104 mmoles) of 2-iminopyrrolidine, resulting in an exothermic temperature rise to 40° C. After stirring for one hour (hr), approximately 75 ml of ethyl acetate was added, and the mixture was extracted with dilute HCl to dissolve the precipitate. The aqueous acidic extract was separated from the organic phase, adjusted to a pH between 4 and 5, and heated on a steam bath for 24 hrs. The solution was adjusted to pH 2, extracted with ether, brought to pH 8, and extracted with methylene chloride. The basic organic phase was chromatographed on silica, eluting with 4% methanol in methylene chloride. The residue obtained on concentration of the pooled fractions was recrystallized from CCl4, melting point (mp) 137.5°-139° C.

Method B.

(a) 1-(4-Fluorophenyl)-2-(2-iminopyrrolidin-1-yl)-ethanone hydrocholoride (Formula (H) compound A stirred solution of 37.3 g (216 mmoles) of 2-chloro-1-(fluorophenyl)-ethanone (prepared as described by Joshi et al., *J. Heterocyclic Chem.* 16, 1141 (1979)) in 70 ml of chloroform chilled in a methanol-ice bath between 15°-18° C., was treated with a solution of 20 g (238 mmoles) of 2-imino-pyrrolidine in 50 ml of chloroform at such a rate as to maintain the temperature of the reaction mixture. After an additional 2 hours, the mixture was triturated with 300 ml Et$_2$O, filtered, and the crystals were washed with ether and recrystallized from alcohol to give white needles of the named Formula (H) compound, mp 207°-208° C.

Anal. Calcd. for $C_{12}H_{14}Cl\ F\ N_2O$: C, 56.15; H, 5.50; N, 10.91. Found: C, 56.14; H, 15.50; N, 10.90.

(b) 2-(4-Fluorophenyl)-6,7-dihydro-(5H)-pyrrolo [1,2-a]imidazole (Formula (E) Compound)

An aqueous solution of 31 g (0.12 mole) of the named Formula (H) compound of Method B, part a above, was heated in 300 ml of water on a steam bath for 8 hours. The solution was adjusted to pH 6.5, and the resulting precipitate was filtered, dried under vacuum and recrystallized from CCl4 to give the named Formula (E) compound, mp 137.5°-139° C.

Anal. Calcd. for $C_{12}H_{11}FN_2$: C, 71.27; H, 5.48; N, 13.85.

Found: C, 71.00; H, 5.61; N, 13.73.

EXAMPLE II 2-(4-fluorophenyl)-3-(4-pyridyl)-6,7-dihydro-[5H]-pyrrolo [1,2-a]imidazole (Formula (I) Compound)

A stirred solution of 13.1 g (0.065 mole) of 2-(4-fluorophenyl)-6,7-dihydro-[5H]-pyrrolo[1,2-a]imidazole, prepared as described in Example I, and 51.4 g (0.65 mole) of dry pyridine in 17 ml of dry methylene chloride at 22°-25° C. was treated over 1.5 hours (hr) with 35.3 g (0.325 mmole) of ethyl chloroformate. The solution was stirred at 25° C. overnight, and the treatment with pyridine and ethyl chloroformate repeated as before, followed by a 24 hr period of stirring. After 3 more treatments as described above, the solvent was removed in vacuo. The residue was dissolved in 5% aqueous NaHCO$_3$ and extracted into methylene chloride. The organic phase was washed with 5% aqueous NaHCO$_3$ and dried over anhydrous K$_2$CO$_3$. The volatile solvents were removed in vacuo and the residue extracted into methylene chloride. The organic phase was extracted repeatedly with 0.2 M HCl until traces of starting material were removed, then washed with 5% Na$_2$CO$_3$ solution, dried over K$_2$CO$_3$ (anhydrous), and striped in vacuo. The residue was crystallized from toluene-hexane to give the compound of Formula (F) known as 3-(N-ethoxycarbonyl-1,4-dihydro-4-pyridyl)-

2-(4-fluoro-phenyl)-6,7dihydro[5H]-pyrrolo(1,2-a]imidazole, 146°–147° C.

Method A.

0.5 g (1.4 mmoles) of the Formula (F) product described in Example II was heated with stirring in 5 ml of decalin under argon. Upon reaching a temperature of 80° C., 0.06 g (1.8 mmoles) of sulfur was added and the mixture heated to 165° C. until starting material was consumed. The cooled mixture was filtered and the solid washed with petroleum ether and dissolved in chloroformethyl acetate (1:1). This solution was decolorized with Darco, and chromatographed on silica. Elution with 20% methanol in chloroform-ethyl acetate (1:1) afforded a fraction which was concentrated in vacuo, and recrystallized from carbon tetrachloride to give the desired Example II title product, mp 163°–164.5° C.

Method B.

15.0 g (42.4 mmoles) of a Formula (F) compound, i.e., 3-(N-ethoxycarbonyl-1,4-dihydro-4-pyridyl)-2-(4-fluorophenyl)-6,7-dihydro[5H]-pyrrolo[1,2-a]imidazole, prepared as described above, was added to a stirred solution of 28.6 g (255 mmoles) of potassium tert.-butoxide dissolved in tert.-butanol (250 ml) into which $O_2$ was being bubbled. The solution was heated to reflux for 15 minutes, and the solvent then removed in vacuo. The solid product was extracted into methylene chloride, washed with water and then extracted into aqueous 3N HCl. This aqueous acidic phase was made basic with cold 10% aqueous sodium hydroxide and extracted with methylene chloride. The resulting organic phase was dried over anhydrous $K_2CO_3$ and the solvent was removed in vacuo. Two recrystallizations from toluene gave the Example II title product, mp 165°–166° C.

Anal Calcd. for $C_{17}H_{14}FN_3$:C, 73.10; H, 5.05; N, 15.04. Found: C, 73.31; H, 5.11; N, 15.08.

EXAMPLE III 3-(N-ethyloxycarbonyl-1,4-dihydro-4-pyridyl)-2-(4-methoxyphenyl)-6,7-dihydro-[5H]-pyrrolo[1,2-a]imidazole (Formula (F) Compound)

a. 2-(4-Methoxyphenyl)-6,7-dihydro-[5H]-pyrrolo [1,2-a]imidazole (Formula (E) Compound).

To a solution of 6.8 g (29.7 mmoles) of 2-bromo-4-methoxyacetophenone in 50 ml of $CHCl_3$ was added a solution of 5 g (59.4 mmoles) of 2-iminopyrrolidine in 30 ml of $CHCl_3$ with chilling. After 4 hours of stirring at 25° C., the solvent was removed in vacuo. The residue was dissolved in water, the pH adjusted to 2.5 and the solution heated on a steam bath under argon atmosphere for 8 hours. The cooled solution was adjusted to pH 6. The resulting precipitate, filtered, washed with water and dried in vacuo to afford the titled compound, mp 116°–117.5° C.

b. 3-(N-Ethyloxycarbonyl-1,4-dihydro-4-pyridyl)-2-(4-methoxyphenyl)-6,7-dihydro-[5H]-pyrrolo[1,2-a]imidazole A stirred solution of 2.8 g (13.1 mmoles) of 2-(4-methoxyphenyl)-6,7-dihydro-[5H]-pyrrolo[1,2-a]imidazole, prepared as described above, and 6.2 g (78.4 mmoles) of dry pyridine in 30 ml of dry $CH_2Cl_2$ was treated dropwise over 1 hour at 5° C. under argon atmosphere with 4.25 g (39.2 mmoles) of ethyl chloroformate. After stirring for 1 hour an additional 3.1 g (39.2 mmoles) of pyridine was added, followed by 2.15 g (19.8 mmoles) of ethyl chloroformate added over 2 hours. The mixture was stirred overnight at 25° C., then poured into ice water made alkaline with $Na_2CO_3$ and extracted with $CH_2Cl_2$. The organic phase was sequentially washed with 0.2 N HCl, water, and aqueous $K_2CO_3$ solution, dried over $Na_2SO_4$ and stripped in vacuo to afford the titled compound as an amber resin.

EXAMPLE IV 2-(4-methoxyphenyl)-3-(4-pyridyl)-6,7-dihydro-[5H]-pyrrolo [1,2-a]imidazole (Formula (I) Compound)

4.1 g (11.2 mmole) of the named compound described in Example III, prepared as described in Example III, was heated with stirring in 25 ml of decalin under argon. Upon reaching 85° C., the solid was dissolved, and 0.468 g (14.6 mmoles) of sulfur was added. The mixture was heated to 165° C. and another 0.235 g (7.3 mmoles) of sulfur was added. After another 45 minutes, the starting material was consumed, and the cooled reaction mixture was diluted with 25 ml of petroleum ether and filtered. The filtered solid was washed with additional petroleum ether, dissolved in $CHCl_3$-EtOAc and chromatographed on silica. The material eluting with 8 to 25% methanol in $CHCl_3$-EtOAc (1:1) was concentrated in vacuo and recrystallized from toluene-cyclohexane to give the desired product, mp 157.5°–158.5° C.;

Anal. Calcd. for $C_{18}H_{17}N_3O$:C, 74.20; H, 5.88; N, 14.42. Found: C, 74.09; H, 5.88; N, 14.45.

EXAMPLE V

3-Bromo-2-(4-fluorophenyl)-6,7-dihydro-[5H]-pyrrolo[1,2-a]imidazole (Formula (G) Compound)

A stirred solution of 100 mg (0.50 mmole) of 2-(4-fluorophenyl)-6,7-dihydro-[5H]-pyrrolo[1,2-a]imidazole, prepared as described in Example I, was treated dropwise with a solution of 90 mg (0.56 mmole) of bromine in 0.5 ml of methylene chloride. After 45 minutes, the solution was made basic with 5% aqueous NaOH and dried organics over anhydrous $K_2CO_3$. The solvent was removed in vacuo, and the residue was recrystallized from carbon tetrachloride-hexane to give the desired Example V title product, mp 188°–189° C. dec.

UTILITY EXAMPLES

In the following Examples male Balb/c mice (20–28 g), were used. All mice were obtained from Charles River Breeding Laboratories, Kingston, N.Y. Within a single experiment, mice were age matched.

In the following examples, reagents used were employed as follows:

Compounds of Formula (I) were each used as the free base. The compounds were homogenized in 0.5% tragacanth. Compounds were administered by lavage at the indicated dose in a final volume of 10 ml/kg.

For in vitro experiments, compounds were dissolved at appropriate concentrations in ethanol (final concentration 1.0%) and then diluted to final concentrations using the buffers indicated in the text.

I. METHODS

Arachidonic Acid-Induced Mouse Ear Inflammation

Arachidonic acid in acetone (2 mg/20 ul) was applied to the inner surface of the left ear. The thickness of both ears was then measured with a dial micrometer one hour after treatment, and the data were expressed as the change in thickness ($10^{-3}$ cm) between treated and untreated ears.

Test compounds were given orally in 0.5% tragacanth at the times indicated in the text prior to the topical application of arachidonic acid.

Assay of 5-Lipoxygenase Activities

The activities of these enzymes in extracts of RBL-1 cells were assayed using the method of Jakschik and Lee, Nature, 287, 51–52 (1980). RBL-1 cells were obtained from the American Type Culture Collection (#CRL 1378) and were grown at 37° C. (5% $CO_2$ in air) in spinner culture in MEM supplemented with 10% heat inactivated fetal calf serum. Harvested cells were washed with 50 mM sodium phosphate buffer, pH 7.0, containing 1 mM EDTA and 0.1% gelatin, resuspended in fresh buffer ($5 \times 10^7$ cells/ml) and disrupted by nitrogen cavitation using the Parr bomb at 750 psi for 10 min. The broken cell extract was then centrifuged at $10,000 \times g$ for 20 minutes (min) and the supernatant was centrifuged at $100,000 \times g$ for 60 min. Aliquots (0.25 mls) of the supernatant were preincubated with or without drugs for 10 min, after which 10 ul $CaCl_2$ (2 mM) was added and the reaction was initiated with 2.5 ul of 2.5 mM arachidonic acid-1-$^{14}$C (final concentration was 25 uM; specific activity 20,000 dpm/nmole). After incubation for 5 min at 37° C., the reaction was terminated by addition of 2 volumes (0.5 ml) ice cold acetone and the sample was allowed to deproteinize on ice for 10 min prior to centrifugation at $1,000 \times g$ for 10 min. The deproteinized supernatant was adjusted to pH 3.5 with 2N formic acid and extracted with 2 volumes of ice cold ethyl acetate. The extracted samples were dried under argon, redissolved in ethyl acetate and applied to Whatman LK5D thin layer chromatography (TLC) plates which were developed using the A-9 solvent system [organic phase of ethyl acetate: 2,2,5-trimethylpentane:acetic acid: water (110:50:20:10)] described by Hamberg and Samuelsson, J. Biol. Chem., 241, 257–263 (1966). Arachidonic acid, 5-HETE, $LTB_4$ and $PGD_2$ were quantified with a Berthold LB 2832 autoscanner.

Under these conditions, only the 5-lipoxygenase pathway metabolites were detectable. The 5-HETE and di-HETEs were formed at a linear rate, and substantial amounts of the arachidonic acid-1-$^{14}$C substrate were utilized.

Drug-induced effects on enzyme activities are described as the concentration of drug causing a 50% inhibition of metabolite synthesis ($IC_{50}$)

LTC-4 Production by Human Monocytes

Human monocytes were prepared from whole blood supplied by the American Red Cross. The blood was fractionated by a two-step procedure employing sedimentation on Ficoll follwed by sedimentation on Percoll. The mononuclear cell fraction recovered was composed of 80–90% monocytes with the remainder of the cells being predominantly lymphocytes. The monocytes were plated at $1 \times 10^6$ cells per well in a Costar 24 well tissue culture plate and allowed to adhere for 1 hour at 37°. Non-adherent cells were removed by washing the cells were stimulated with 1 uM A23187 calcium ionophore for 3 hours at 37° to induce LTC-4 production when drugs were evaluated. They were added to the cells 30 minutes prior to the A23187. Supernatants were collected, clarified by centrifugation and store frozen at −20° C. until assay. The LTC-4 content was determined by using a New England Nuclear Leukotriene C-4 ($^3$H) RIA Kit as per instructions.

II. RESULTS

The Effect of Compounds of Formula (I) on Arachidonic Acid-induced Inflammation Elucidation of the antiinflammatory activity of the compounds of Formula (IA) was achieved in a model of arachidonic acid-induced edema in mice. The mouse ear edematous response to arachidonic acid has been shown to be sensitive to agents that inhibit both lipoxygenase- and cyclooxygenase-generated mediators or that selectively inhibit lipoxygenase, but not cyclooxygenase, enzyme activity [See, Young et al., J. Invest. Dermatol., 82, 367–371 (1984)]. Compounds of Formula (IA) produced marked inhibition of the edematous response normally seen 1 hour after the application of 2 mg of arachidonic acid to the ear (Table I). The activity of compounds of Formula (IA) in this assay is greater than for phenidone ($ED_{50}=44.0$ mg/kg, p.o.). The cyclooxygenase inhibitors, indomethacin (10 mg/kg, p.o.), ibuprofen (250 mg/kg, p.o.) and naproxen (100 mg/kg, p.o.) do not exhibit detectable antiinflammatory activity in this assay.

These findings indicate that compounds of Formula (IA) are potent inhibitors of both the cellular and edematous responses of inflammation in mice. These inflammatory responses were also inhibited by agents that inhibit lipoxygenase activity but not by selective cyclooxygenase inhibitors.

The Effect of Compounds of Formula (IA) on Arachidonic Acid Metabolism

Experiments using a soluble extract preparation of RBL-1 cells containing only lipoxygenase activity confirmed the inhibitory effects of compounds of Formula (IA) on $LTB_4$ production (Table II). Indomethacin at concentrations up to $10^{-4}$M was inactive. The data presented in Table II indicate that compounds of Formula (IA) are inhibitors of the 5-lipoxygenase pathway as confirmed by their ability to inhibit $LTB_4$, a 5-lipoxygenase pathway product. The data presented in Table III indicate that compounds of Formula (IA) are inhibitors of the 5-lipoxygenase pathway as confirmed by their ability to inhibit 5-HETE, a 5-lipoxygenase pathway product.

$LTC_4$ Inhibition Assay

As shown in Table IV, compounds of Formula (IA) were efficacious in inhibiting $LTC_4$ production, a 5-lipoxygenase pathway product, by human monocytes. These data confirm the ability of compounds of Formula (IA) to inhibit the 5-lipoxygenase pathway.

TABLE I

The Effect of Compounds of Formula (IA) on Arachidonic Acid Induced Ear Swelling

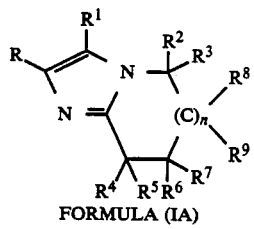

FORMULA (IA)

| Compound Number | R | $R^1$ | $R^2$ | $R^3$ | $R^4$ | $R^5$ | $R^6$ | $R^7$ | $R^8$ | $R^9$ | n | % Inhibition of Ear Swelling[a,b] |
|---|---|---|---|---|---|---|---|---|---|---|---|---|
| 1 | 4-fluorophenyl | 4-pyridyl | H | H | H | H | H | H | — | — | 0 | 93 |
| 2 | 4-methoxyphenyl | 4-pyridyl | H | H | H | H | H | H | — | — | 0 | 83 p.o. |

[a] screened at 50 mg/kg s.c. or i.p. unless indicated as oral dosing (p.o.).
[b] * = p .05,  = p .01, * = p .001, NS = not significant.

TABLE II

The Effect of Compounds of Formula (IA) on 5-Lipoxygenase Activity ($LTB_4$ Production)

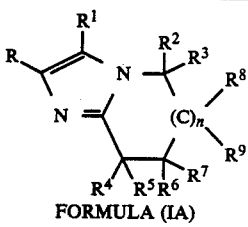

FORMULA (IA)

| Compound Number | R | $R^1$ | $R^2$ | $R^3$ | $R^4$ | $R^5$ | $R^6$ | $R^7$ | $R^8$ | $R^9$ | n | 5-LO[a] $IC_{50}$ (uM) |
|---|---|---|---|---|---|---|---|---|---|---|---|---|
| 1 | 4-fluorophenyl | 4-pyridyl | H | H | H | H | H | H | — | — | 0 | 32 |
| 2 | 4-methoxyphenyl | 4-pyridyl | H | H | H | H | H | H | — | — | 0 | 10 |

[a] $IC_{50}$ determined on $LTB_4$ production by RBL-1 high speed supernatant.

TABLE III

The Effect of Compounds of Formula (IA) on 5-Lipoxygenase Activity (5-HETE Production)

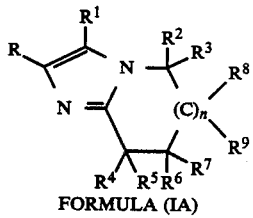

FORMULA (IA)

| Compound Number | R | $R^1$ | $R^2$ | $R^3$ | $R^4$ | $R^5$ | $R^6$ | $R^7$ | $R^8$ | $R^9$ | n | 5-LO[a] $IC_{50}$ (uM) |
|---|---|---|---|---|---|---|---|---|---|---|---|---|
| 1 | 4-fluorophenyl | 4-pyridyl | H | H | H | H | H | H | — | — | 0 | 67 |
| 2 | 4-methoxyphenyl | 4-pyridyl | H | H | H | H | H | H | — | — | 0 | 16 |

[a] $IC_{50}$ determined on 5-HETE production by RBL-1 high speed supernatant.

TABLE IV

The Effect of Compounds of Formula (IA) on 5-Lipoxygenase Activity ($LTC_4$ Production)

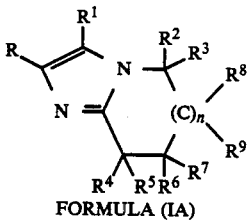

FORMULA (IA)

| Compound Number | R | $R^1$ | $R^2$ | $R^3$ | $R^4$ | $R^5$ | $R^6$ | $R^7$ | $R^8$ | $R^9$ | n | 5-LO[a] $IC_{50}$ (uM) |
|---|---|---|---|---|---|---|---|---|---|---|---|---|
| 1 | 4-fluorophenyl | 4-pyridyl | H | H | H | H | H | H | — | — | 0 | 0.1–2.1 |

TABLE IV-continued

The Effect of Compounds of Formula (IA) on 5-Lipoxygenase Activity (LTC$_4$ Production)

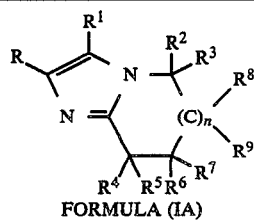

FORMULA (IA)

| Compound Number | R | R$^1$ | R$^2$ | R$^3$ | R$^4$ | R$^5$ | R$^6$ | R$^7$ | R$^8$ | R$^9$ | n | 5-LO[a] IC$_{50}$ (uM) |
|---|---|---|---|---|---|---|---|---|---|---|---|---|
| 2 | 4-methoxyphenyl | 4-pyridyl | H | H | H | H | H | H | — | — | 0 | NT[b] |

[a]IC$_{50}$ determined on LTC$_4$ production by human monocytes.
[b]NT = not tested

COMPOSITION EXAMPLES

EXAMPLE A—CAPSULE COMPOSITION

A pharamceutical composition of this invention in the form of a capsule is prepared by filling a standard two-piece hard gelatin capsule with 50 mg. of a compound of Formula (IA), in powdered form, 110 mg. of lactose, 32 mg. of talc and 8 mg. of magnesium stearate.

EXAMPLE B—INJECTABLE PARENTERAL COMPOSITION

A pharmaceutical composition of this invention in a form suitable for administration by injection is prepared by stirring 1.5% by weight of a compound of Formula (IA) in 10% by volume propylene glycol and water. The solution is sterilized by filtration.

EXAMPLE C—OINTMENT COMPOSITION

Compound of Formula (IA) 1.0 g
White soft paraffin to 100.0 g

The compound of Formula (IA) is dispersed in a small volume of the vehicle and this dispersion is gradually incorporated into the bulk to produce a smooth, homogeneous product which is filled into collapsible metal tubes.

EXAMPLE D—TOPICAL CREAM COMPOSITION

Compound of Formula (IA) 1.0 g
Polawax GP 200 20.0 g
Lanolin Anhydrous 2.0 g
White Beeswax 2.5 g
Methyl hydroxybenzoate 0.1 g
Distilled Water to 100.0 g The polawax, beeswax and lanolin are heated together at 60° C. and added to a solution of methyl hydroxybenzoate. Homogenization is achieved using high speed stirring and the temperature is allowed to fall to 50° C. The compound of Formula (IA) is added and dispersed throughout, and the composition is allowed to cool with slow speed stirring.

EXAMPLE E—TOPICAL LOTION COMPOSITION

Compound of Formula (1A) 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml The methyl hydroxybenzoate and glycerin are dissolved in 70 ml of the water at 75°. The sorbitan monolaurate, polysorbate 20 and cetostearyl alcohol are melted together at 75° C. and added to the aqueous solution. The resulting emulsion is homogenized, allowed to cool with continuous stirring and the compound of Formula (IA) is added as a suspension in the remaining water. The whole suspension is stirred until homogenized.

EXAMPLE F—EYE DROP COMPOSITION

Compound of Formula (IA) 0.5 g
Methyl Hydroxybenzoate 0.01 g
Propyl Hydroxybenzoate 0.04 g
Purified Water B.P. to 100.00 ml The methyl and propyl hydroxybenzoates are dissolved in 70 ml purified water at 75° C. and the resulting solution is allowed to cool. The compound of Formula (IA) is then added, and the solution is made up to 100 ml with purified water. The solution is sterilized by filtration through a membrane filter (0.22 mu m pore size) and packed aseptically into suitable sterile containers.

EXAMPLE G—COMPOSITION FOR ADMINISTRATION BY INHALATION

For an aerosol container with a capacity of 15–20 ml: Mix 10 mg of a compound of Formula (IA) with 0.1–0.2% of a lubricating agent, such as Span 85 or oleic acid, and disperse such mixture in a propellant (c.a.), such as freon, preferably a combination of freon 114 and freon 12, and put into an appropriate aerosol container adapted for either intranasal or oral inhalation administration.

EXAMPLE H—COMPOSITION FOR ADMINISTRATION BY INHALATION

For an aerosol container with a capacity of 15–20 ml: Dissolve 10 mg of a compound of Formula (IA) in ethanol (6–8 ml), add 0.1–0.2% of a lubricating agent, such as Span 85 or oleic acid, and disperse such in a propellant (c.a.), such as freon, preferably a combination of freon 114 and freon 12, and put into an appropriate aerosol container adapted for either intranasal or oral inhalation administration.

What is claimed is:
1. A compound of the formula

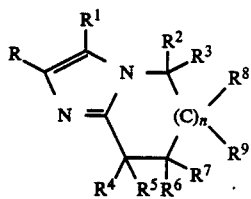

FORMULA (I)

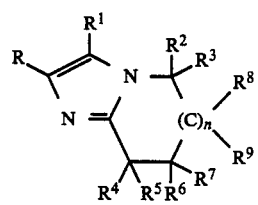

FORMULA (IA)

wherein:
n is 0 or 1;
one of R or $R^1$ must be pyridyl and the other is selected from:
(a) monosubstituted phenyl wherein said substituent is selected from H, halo, $C_{1-3}$ alkoxy, $C_{1-3}$ alkylthio, $C_{1-4}$ alkyl, $C_{1-3}$ alkylsulfinyl, $C_{1-3}$ alkylsulfonyl, $C_{1-3}$ alkylamino, $C_{1-3}$ dialkylamino, $CF_3$, [N-($C_{1-3}$ alkyl)-N-($C_{1-3}$ alkanamido),] N-(azacyclo $C_{5-6}$ alkyl), prop-2-ene-1-oxy or 2,2,2-trihaloethoxy;
(b) disubstituted phenyl wherein said substituents are the same and are selected from halo, $C_{1-3}$ alkoxy, $C_{1-3}$ alkylamino, $C_{1-3}$ dialkylamino, N-(azacyclo $C_{5-6}$ alkyl), 2,2,2-trihaloethoxy, prop-2-ene-1-oxy, or the disubstituents together form a methylene dioxy group; or
(c) disubstituted phenyl wherein said substituents are not the same and are independently selected from $C_{1-3}$ alkylamino, $C_{1-3}$ dialkylamino, or N-(azacyclo $C_{5-6}$ alkyl); and
(d) disubstituted phenyl wherein one of said substituents must be $C_{1-3}$ alkoxy, hydroxy, 2,2,2-trihaloethoxy or prop-2-ene-1-oxy and the other substitutent is independently selected from halo, $C_{1-3}$ alkylamino, N-($C_{1-3}$alkyl)-N-$C_{1-3}$alkanamido), $C_{1-3}$dialkylamino, amino, or N-(azacyclo $C_{5-6}$alkyl); and $R^2$, $R^3$, $R^4$, $R^5$, $R^6$, $R^7$, $R^8$ and $R^9$ are H, or one or two of $R^2$, $R^3$, $R^4$, $R^5$, $R^6$, $R^7$, $R^8$ and $R^9$ are independently selected from H or $C_{1-2}$ alkyl; provided that:
(1) when $R^1$ is 2 or 3-pyridyl and R is monosubstituted phenyl, the substituent is selected from other than bromo, iodo, $C_{1-3}$ alkylthio, $C_{1-3}$ alkylsulfinyl or $C_{1-3}$ alkylsulfonyl;
(2) when $R^1$ is 2 or 3-pyridyl and R is disubstituted phenyl, the disubstituents are both selected from other than bromo, or iodo;
(3) when R is 2, 3 or 4-pyridyl and $R^1$ is monosubstituted phenyl, the substituents are selected from other than bromo, iodo, $C_{1-3}$ alkylthio, $C_{1-3}$ alkylsulfinyl, or $C_{1-3}$ alkylsulfonyl; and
(4) when R is 2, 3 or 4-pyridyl and $R^1$ is disubstituted phenyl, the substituents are both selected from other than bromo, or iodo;
or a pharmaceutically acceptable salt thereof.

2. The compound of claim 1 wherein $R^1$ is 4-pyridyl, R is 4-fluorophenyl, n is O, and $R^2$, $R^3$, $R^4$, $R^5$, $R^6$ and $R^7$ are all H.

3. The compound of claim 1 wherein R is 4-methoxyphenyl, $R^1$ is 4-pyridyl, n is O and $R^2$, $R^3$, $R^4$, $R^5$, $R^6$ and $R^7$ are all H.

4. A pharmaceutical composition comprising a pharmaceutically acceptable carrier or diluent and an effective, non-toxic 5-lipoxygenase pathway inhibiting amount of a compound of the formula wherein:
n is 0 or 1;
One of R or $R^1$ must be pyridyl and the other is selected from:
(a) monosubstituted phenyl wherein said substituent is selected from H, halo, $C_{1-3}$ alkoxy, $C_{1-3}$ alkylthio, $C_{1-4}$ alkyl, $C_{1-3}$ alkylsulfinyl, $C_{1-3}$ alkylsulfonyl, $C_{1-3}$ alkylamino, $C_{1-3}$ dialkylamino, $CF_3$, N-(azacyclo $C_{5-6}$ alkyl), prop-2-ene-1-oxy or 2,2,2-trihaloethoxy;
(b) disubstituted phenyl wherein said substituents are the same and are selected from halo, $C_{1-3}$ alkoxy, $C_{1-3}$ alkylamino, $C_{1-3}$ dialkylamino, N-(azacyclo $C_{5-6}$ alkyl), 2,2,2-trihaloethoxy, prop-2-ene-1-oxy, or the disubstituents together form a methylene dioxy group; or
(c) disubstituted phenyl wherein said substituents are not the same and are independently selected from $C_{1-3}$ alkylamino, $C_{1-3}$ dialkylamino, or N-(azacyclo $C_{5-6}$ alkyl), or
(d) disubstituted phenyl wherein one of said substituents must be $C_{1-3}$ alkoxy, hydroxy, 2,2,2-trihaloethoxy or prop-2-ene-1-oxy and the other substituent is independently selected from halo, $C_{1-3}$ alkylamino, N-($C_{1-3}$ alkyl)-N-($C_{1-3}$ alkanamido), $C_{1-3}$ dialkylamino, amino, or N-(azacyclo $C_{5-6}$ alkyl); and $R^2$, $R^3$, $R^4$, $R^5$, $R^6$, $R^7$, $R^8$ and $R^9$ are H or one or two of $R^2$, $R^3$, $R^4$, $R^5$, $R^6$, $R^7$, $R^8$ and $R^9$ are independently selected from H or $C_{1-2}$ alkyl; provided that:
(1) when $R^1$ is 2 or 3-pyridyl and R is monosubstituted phenyl, the substituent is selected from other than bromo, iodo, $C_{1-3}$ alkylthio, $C_{1-3}$ alkylsulfinyl, or $C_{1-3}$ alkylsulfonyl;
(2) when $R^1$ is 2 or 3-pyridyl and R is disubstituted phenyl, the disubstituents are both selected from other than bromo or iodo;
(3) when R is 2, 3 or 4-pyridyl and $R^1$ is monosubstituted phenyl, the substituents are selected from other than bromo, iodo, $C_{1-3}$ alkylthio, $C_{1-3}$ alkylsulfinyl, or $C_{1-3}$ alkylsulfonyl; and
(4) when R is 2, 3 or 4-pyridyl and $R^1$ is disubstituted phenyl, the substituents are both selected from other than bromo or iodo;
or a pharmaceutically acceptable salt thereof.

5. The composition of claim 4 wherein $R^1$ is 4-pyridyl, R is 4-fluorophenyl, n is O, and $R^2$, $R^3$, $R^4$, $R^5$, $R^6$ and $R^7$ are all H.

6. The composition of claim 4 wherein R is 4-methoxyphenyl, $R^1$ is 4-pyridyl, n is O and $R^2$, $R^3$, $R^4$, $R^5$, $R^6$ and $R^7$ are all H.

7. The composition of claim 4 wherein the composition is in dosage unit form adapted for parenteral administration.

8. The composition of claim 4 wherein the composition is in dosage unit form adapted for oral administration.

9. The composition of claim 7 which comprises from about 50 mg to about 500 mg of the compound.

10. The composition of claim 8 which comprises from about 100 mg to about 1000 mg of the compound.

11. The composition of claim 4 wherein the composition is in a dosage unit form adapted for administration by inhalation.

12. The composition of claim 4 wherein the composition is in a dosage unit form adapted for topical administration.

13. A method of treating a 5-lipoxygenase pathway mediated disease in an animal in need thereof which comprises administering to such animal an effective, non-toxic 5-lipoxygenase pathway inhibiting amount of a compound of the formula:

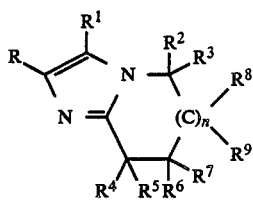

FORMULA (IA)

wherein:
n is 0 or 1;
One of R or $R^1$ must be pyridyl and the other is selected from:
(a) monosubstituted phenyl wherein said substitutent is selected from H, halo, $C_{1-3}$ alkoxy, $C_{1-3}$ alkylthio, $C_{1-4}$ alkyl, $C_{1-3}$ alkylsulfinyl, $C_{1-3}$ alkylsulfonyl, $C_{1-3}$ alkylamino, $C_{1-3}$ dialkylamino, $CF_3$, N-(azacyclo $C_{5-6}$ alkyl), prop-2-ene-1-oxy or 2,2,2-trihaloethoxy;
(b) disubstituted phenyl wherein said substituents are the same and are selected from halo, $C_{1-3}$ alkoxy, $C_{1-3}$ alkylamino, $C_{1-3}$ dialkylamino, N-(azacyclo $C_{5-6}$ alkyl), 2,2,2-trihaloethoxy, prop-2-ene-1-oxy, or the disubstituents together form a methylene dioxy group; or
(c) disubstituted phenyl wherein said substituents are not the same and are independently selected from $C_{1-3}$ alkylamino, $C_{1-3}$ dialkylamino, or N-(azacyclo $C_{5-6}$ alkyl); or
(d) disubstituted phenyl wherein one of said substituents must be $C_{1-3}$ alkoxy, hydroxy, 2,2,2-trihaloethoxy or prop-2-ene-1-oxy and the other substituent is independently selected from halo, $C_{1-3}$ alkylamino, N-($C_{1-3}$ alkyl)-N-($C_{1-3}$ alkanamido), $C_{1-3}$ dialkylamino, amino, or N-(azacyclo $C_{5-6}$ alkyl); and $R^2$, $R^3$, $R^4$, $R^5$, $R^6$, $R^7$, $R^8$ and $R^9$ are H or one or two of $R^2$, $R^3$, $R^4$, $R^5$, $R^6$, $R^7$, $R^8$ and $R^9$ are independently selected from H or $C_{1-2}$ alkyl; provided that:
(1) when $R^1$ is 2 or 3-pyridyl and R is monosubstituted phenyl, the substituent is selected from other than bromo, iodo, $C_{1-3}$ alkylthio, $C_{1-3}$ alkylsulfinyl, or $C_{1-3}$ alkylsulfonyl;
(2) when $R^1$ is 2 or 3-pyridyl and R is disubstituted phenyl, the disubstituents are both selected from other than bromo or iodo;
(3) when R is 2, 3 or 4-pyridyl and $R^1$ is monosubstituted phenyl, the substituents is selected from other than bromo, iodo, $C_{1-3}$ alkylthio, $C_{1-3}$ alkylsulfinyl, or $C_{1-3}$ alkylsulfonyl; and (4) when R is 2, 3 or 4-pyridyl and $R^1$ is disubstituted phenyl, the substituents are both selected from other than bromo or iodo;
or a pharmaceutically acceptable salt thereof.

14. The method of claim 13 wherein $R^1$ is 4-pyridyl, R is 4-fluorophenyl, n is 0, $R^2$, $R^3$, $R^4$, $R^5$, $R^6$ and $R^7$ are all H.

15. The method of claim 13 wherein R is 4-methoxyphenyl, $R^1$ is 4-pyridyl, n is O, and $R^2$, $R^3$, $R^4$, $R^5$, $R^6$ and $R^7$ are all H.

16. The method of claim 14 wherein the administration is parenteral and the amount of compound administered per dosage unit form is selected from about 50 mg to about 500 mg.

17. The method of claim 15 wherein the administration is oral and the amount of compound administered per oral dosage unit form is selected from about 100 mg to about 1000 mg.

18. The method of claim 13 wherein the administration is parenteral and the amount of compound administered per day is from about 50 mg to about 1000 mg.

19. The method of claim 13 wherein the administration is oral and the amount of compound administered per day is from about 150 mg to about 2000 mg.

20. The method of claim 13 wherein the compound is administered by inhalation.

21. The method of claim 20 wherein the amount of compound administered is from about 10 mg to about 100 mg per day.

22. The method of claim 13 wherein the compound is administered topically.

23. The method of claim 20 wherein the amount of compound administered per dose is 1 ug to 1000 ug.

24. A compound of the formula wherein

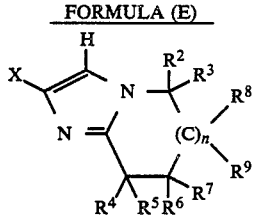

FORMULA (E)

n is 0 or 1;
$R^2$, $R^3$, $R^4$, $R^5$, $R^6$, $R^7$, $R^8$ and $R^9$ are H, or one or two of $R^2$, $R^3$, $R^4$, $R^5$, $R^6$, $R^7$, $R^8$ and $R^9$ are independently selected from H or $C_{1-2}$ alkyl;
X is selected from:
(a) pyridyl;
(b) monosubstituted phenyl, wherein said substituent is selected from halo, $C_{1-3}$ alkoxy, amino, hydroxy, $C_{1-3}$ alkylthio, $C_{1-4}$ alkyl, N-($C_{1-3}$ alkyl)-N-($C_{1-3}$ alkanamido), N-($C_{1-3}$ alkanamido), $C_{1-3}$ alkylamino, $C_{1-3}$ dialkylamino, $CF_3$, N-(azacyclo $C_{5-6}$ alkyl), prop-2-ene-1-oxy or 2,2,2-trihaloethoxy;
(c) disubstituted phenyl wherein said substituents are the same and are selected from halo, $C_{1-3}$ alkoxy, $C_{1-3}$ alkylamino, $C_{1-3}$ dialkylamino, amino, N-(azacyclo $C_{5-6}$ alkyl), 2,2,2-trihaloethoxy, prop-2-ene-1-oxy, hydroxy, or the disubstituents together form a methylene dioxy group; or
(d) disubstituted phenyl wherein said substituents are not the same and are independently selected from halo, $C_{1-3}$ alkylamino, $C_{1-3}$ dialkylamino, amino, N-(azacyclo C$_{5-6}$ alkyl), nitro, N-(C$_{1-3}$ alkanamido), or N-(C$_{1-3}$ alkyl)-N-(C$_{1-3}$ alkanamido), or (e) disubstituted phenyl wherein one of said substituents must be C$_{1-3}$ alkoxy, hydroxy, 2,2,2-trihaloethoxy or prop-2-ene-1-oxy and the other substituent is independently selected from halo, C$_{1-3}$ alkylamino, nitro, N-(C$_{1-3}$ alkyl)-N-(C$_{1-3}$ alkanamido), C$_{1-3}$ dialkylamino, amino, or N-(azacyclo C$_{5-6}$ alkyl); provided that when n is 1 and R$^2$, R$^3$, R$^4$, R$^5$, R$^6$, R$^7$, R$^8$ and R$^9$ are H, X is other than 2,4-dimethoxyphenyl or 4-aminophenyl;

or a pharmaceutically acceptable salt thereof.

25. The compound of claim 24 wherein X is 4-fluorophenyl, n is O, and R$^2$, R$^3$, R$^4$, R$^5$, R$^6$, R$^7$, are H.

26. The compound of claim 24 wherein X is 4-methoxyphenyl, n is O, and R$^2$, R$^3$, R$^4$, R$^5$, R$^6$, R$^7$, are H.

27. A compound of the formula:

FORMULA (F)

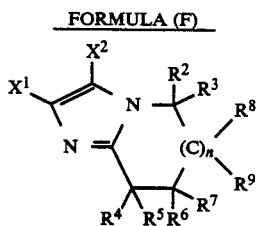

wherein:
n is 0 or 1,
R$^2$, R$^3$, R$^4$, R$^5$, R$^6$, R$^7$, R$^8$, and R$^9$ are all H, or one or two of R$^2$, R$^3$, R$^4$, R$^5$, R$^6$, R$^7$, R$^8$, and R$^9$, are independently selected from H or C$_{1-2}$ alkyl;
X$^2$ is 4-(1,4-dihydro)pyridyl substituted with N-(C$_{1-8}$ alkanoyl), N-(C$_{1-8}$ alkoxycarbonyl), N-(benzoyl), N-(phenoxycarbonyl), N-(phenylacetyl) or N-(benzyloxycarbonyl);
X$^1$ is selected from
(a) monosubstituted phenyl wherein said substituent is selected from H, halo, C$_{1-3}$ alkoxy, C$_{1-3}$ alkylthio, C$_{1-4}$ alkyl, CF$_3$, N-(C$_{1-3}$ alkyl)-N-(C$_{1-3}$ alkanamido), C$_{1-3}$ dialkylamino, CF$_3$, N-(azacyclo C$_{5-6}$ alkyl), prop-2-ene-1-oxy or 2,2,2-trihaloethoxy;
(b) disubstituted phenyl wherein said substituents are the same and are selected from halo, C$_{1-3}$ alkoxy, C$_{1-3}$ dialkylamino, N-(azacyclo C$_{5-6}$ alkyl), 2,2,2-trihaloethoxy, or prop-2-ene-1-oxy, or the disubstituents together form a methylene dioxy group;
(c) disubstituted phenyl wherein said substituents are not the same and are independently selected from halo, nitro, C$_{1-3}$ dialkylamino or N-(C$_{1-3}$ alkyl)-N-(C$_{1-3}$ alkanamido), N-(azacyclo C$_{5-6}$ alkyl); or
(d) disubstituted phenyl wherein one of said substituents must be C$_{1-3}$ alkoxy, hydroxy, 2,2,2-trihaloethoxy or prop-2-ene-1-oxy and the other substituent is independently selected from halo, C$_{1-3}$ alkylamino, nitro, N-(C$_{1-3}$ alkyl)-N-(C$_{1-3}$ alkanamido), C$_{1-3}$ dialkylamino, amino, or N-(azacyclo C$_{5-6}$ alkyl);

or a pharmaceutically acceptable salt thereof.

28. The compound of claim 27 wherein X$^1$ is 4-methoxyphenyl, X$^2$ is N-ethyloxycarbonyl-1,4-dihydro-4-pyridyl, n is O, and R$^2$, R$^3$, R$^4$, R$^5$, R$^6$, R$^7$, are H.

29. The compound of claim 27 wherein X$^2$ is N-ethyloxycarbonyl-1,4-dihydro-4-pyridyl, X$^1$ is 4-fluorophenyl, n is O, and R$^2$, R$^3$, R$^4$, R$^5$, R$^6$, R$^7$, are H.

30. A compound of the formula:

FORMULA (G)

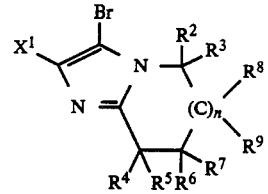

wherein:
n is 0 or 1,
R$^2$, R$^3$, R$^4$, R$^5$, R$^6$, R$^7$, R$^8$ and R$^9$ are all H, or one or two of R$^2$, R$^3$, R$^4$, R$^5$, R$^6$, R$^7$, R$^8$ and R$^9$ are independently selected from H or C$_{1-2}$ alkyl; and
X$^1$ is selected from
(a) monosubstituted phenyl wherein said substituent is selected from H, fluoro, chloro, C$_{1-3}$ alkoxy, C$_{1-4}$ alkyl, C$_{1-3}$ dialkylamino, CF$_3$, C$_{1-3}$ alkylamino, N-(azacyclo C$_{5-6}$ alkyl), prop-2-ene-1-oxy or 2,2,2-trihaloethoxy;
(b) disubstituted phenyl wherein said substituents are the same and are selected from fluoro, chloro, C$_{1-3}$ alkoxy, C$_{1-3}$ dialkylamino, N-(azacyclo C$_{5-6}$ alkyl), 2,2,2-trihaloethoxy, prop-2-ene-1-oxy, or the disubstituents together form a methylene dioxy group; or
(c) disubstituted phenyl wherein said substitutents are not the same and are independently selected from fluoro, chloro, C$_{1-3}$ alkylamino, C$_{1-3}$ dialkylamino, or N-(azacyclo C$_{5-6}$ alkyl); or
(d) disubstituted phenyl wherein one of said substitutents must be C$_{1-3}$ alkoxy, 2,2,2-trihaloethoxy or prop-2-ene-1-oxy and the other substituent is independently selected from fluoro, chloro, C$_{1-3}$ alkylamino, C$_{1-3}$ dialkylamino, or N-(azacyclo C$_{5-6}$ alkyl);

or a pharmaceutically acceptable salt thereof.

31. The compound of claim 30 which is 3-bromo-2-(4-fluorophenyl)-6,7-dihydro-pyrrolo imidazole.

32. A compound of the formula

FORMULA (I)

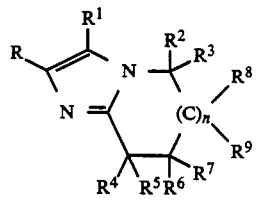

wherein
n is 0 or 1 and R$^1$ is 4-pyridyl and
(a) R is monosubstituted phenyl wherein said substitutent is N-(C$_{1-3}$ alkyl)-N-(C$_{1-3}$ alkanamido);
(b) R is disubstituted phenyl wherein said substituents are the same and are hydroxy; or
(c) R is disubstituted phenyl wherein said substituents are not the same and are independently selected from halo, nitro, N-(C$_{1-3}$ alkyl)-N-(C$_{1-3}$ alkanamido), or amino.

* * * * *

UNITED STATES PATENT AND TRADEMARK OFFICE
CERTIFICATE OF CORRECTION

PATENT NO. : 4,719,218

DATED : January 12, 1988

INVENTOR(S) : Bender, et al.

It is certified that error appears in the above-identified patent and that said Letters Patent is hereby corrected as shown below:

Face page, item (63), first line, change "808,595" to -- 808,407 --.

Column 1, line 9, change "808,595" to -- 808,407 --.

Signed and Sealed this

Twenty-sixth Day of June, 1990

Attest:

HARRY F. MANBECK, JR.

*Attesting Officer*  *Commissioner of Patents and Trademarks*